United States Patent [19]

Hirako

[11] Patent Number: 4,953,979
[45] Date of Patent: Sep. 4, 1990

[54] OPTICAL SYSTEM FOR SIGNAL LIGHT DETECTION IN A FLOW PARTICLE ANALYSIS APPARATUS

[75] Inventor: Shinichi Hirako, Kyoto, Japan
[73] Assignee: Omron Tateisi Electronics Company, Kyoto, Japan
[21] Appl. No.: 271,575
[22] Filed: Nov. 15, 1988
[30] Foreign Application Priority Data

Nov. 18, 1987 [JP] Japan ................ 62-291465

[51] Int. Cl.$^5$ ............................................. G01N 21/53
[52] U.S. Cl. ................................... 356/338; 356/339
[58] Field of Search .............................. 356/338, 339; 250/461.1, 461.2, 574

[56] References Cited

U.S. PATENT DOCUMENTS 4,176,960  12/1979  Eckbreth et al. ............... 356/338
4,577,964  3/1986   Hansen, Jr. ................... 356/338 X Primary Examiner—Davis L. Willis
Assistant Examiner—Matthew W. Koren
Attorney, Agent, or Firm—Dickstein, Shapiro & Morin

[57] ABSTRACT

An optical system for use in a flow particle detection apparatus is disclosed as having a light source for directing light onto flow partricles, a condenser lens for condensing signal light emitted from the flow particles, a photodetector for receiving signal light exiting from the condenser lens, an aperture provided between the condenser lens and the photodetector for removing undesired light, and a convergence-type collimating lens provided between the aperture and the photodetector, the aperture being disposed at a front focal position of the convergence-type collimating lens, and an exit pupil of the condenser lens and a photosensitive surface of the photodetector being located respectively at conjugate points of the convergence-type collimating lens.

5 Claims, 1 Drawing Sheet

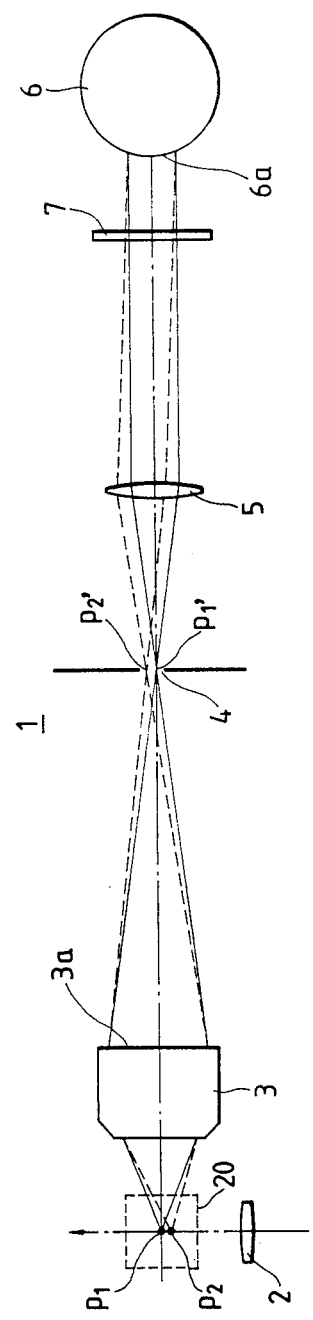
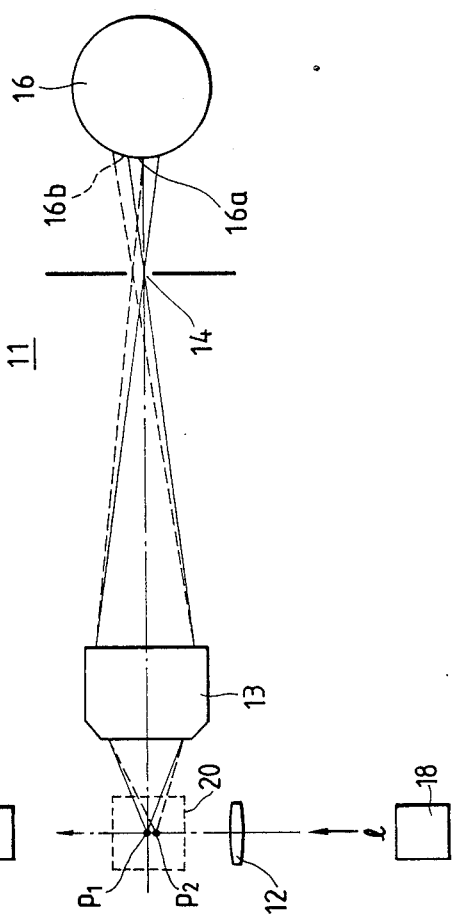
FIG. 1
FIG. 2

OPTICAL SYSTEM FOR SIGNAL LIGHT DETECTION IN A FLOW PARTICLE ANALYSIS APPARATUS

BACKGROUND OF THE INVENTION

1. Field of the Invention

The present invention relates to an optical system for signal light detection in a flow particle analysis apparatus used for cell analysis or the like, and particularly relates to an optical system for signal light detection in which little variation occurs in the output signal of a photodetector even in the case where the position of the flow particles fluctuates.

2. Discussion of the Prior Art

A flow particle analysis apparatus is known which has a flow cell, a light source for illuminating flow particles within the cell, and an optical system for detecting signal light emitted from the flow particles. The flow cell is formed of an optically transparent material (for example, quartz), and a floating liquid of particles to be measured is caused to flow into a measuring flow path formed through the flow cell under the condition that the floating liquid is enclosed by a sheath liquid. The particles to be measured are caused to flow along a central portion of the measuring flow path so as to form one line by hydrodynamic focusing.

The particles to be measured flowing into the flow cell are irradiated with light such as laser light or the like from the light source. At this time, the scattered light generated from the particles to be measured, or fluorescence generated from the particles to be measured in the case where the particles to be measured are dyed with fluorescent pigment, is converged by the signal light detection optical system and converted into an electric signal. The magnitude of the electric signal corresponds to the intensity of the scattered light or fluorescence, and therefore analysis of particles, for example, of a blood cell or the like, can be performed on the basis of the electric signal.

FIG. 2 shows a signal light detection optical system 11 in a conventional flow particle analysis apparatus. In FIG. 2, flow particles $p_1$ are flowing in the direction perpendicular to the paper plane. The flow particles $p_1$ enter a flow cell 20 and are irradiated with laser light 1 from laser source 18 through a condenser lens 12.

Signal light (scattered light or fluorescent light) from the flow particles $p_1$ is converged by a condenser lens 13 and focused on a plane of an aperture 14. The signal light which passes through the aperture 14 strikes a photosensitive surface 16a of a photodetector, for example, a side-on type photomultiplier tube 16 or the like.

In the photodetector, generally, if the incident position of the light varies, the detection sensitivity varies. Accordingly, if the flow particles move away from the central position to a position $p_2$ as shown in FIG. 2, the signal light is displaced as shown by broken lines in FIG. 2 so as to change the incident position 16a of the light onto the photomultiplier tube 16. As a result, a disadvantage occurs in that the magnitude of the output signal of the photomultiplier tube 16 varies correspondingly.

SUMMARY OF THE INVENTION

The present invention has been devised to overcome this problem. An object of the present invention is to provide a signal light detection optical system for a flow particle analysis apparatus in which little variation occurs in the output signal of a photodetector, even when the position of the flow particles fluctuates.

The invention achieves this objective by providing a convergence-type collimating lens between the aperture and photodetector which focuses light from the flow particles onto the same area of the photodetector, even when the position of the flow particles fluctuates.

The above and other objects, features and advantages of the invention will be more clearly understood from the following detailed description of the invention which provided in connection with the accompanying drawings.

BRIEF DESCRIPTION OF THE DRAWINGS

FIG. 1 is a diagram showing an embodiment of the signal light detection optical system for a flow particle analysis apparatus according to the present invention; and, FIG. 2 is a diagram showing the conventional signal light detection optical system for a flow particle analysis apparatus.

DETAILED DESCRIPTION OF THE INVENTION

The arrangement of the signal light detection optical system for a flow particle analysis apparatus according to the present invention will be described with reference to FIG. 1 illustrating one embodiment thereof. The optical system has a condenser lens 3 for condensing signal light emanating from flow particles $p_1$, $p_2$, a photodetector 6 onto which the signal light exiting from the condenser lens 3 is incident, and an aperture 4 provided between the condenser lens 3 and the photodetector 6 for removing undesired light. A convergence-type collimating lens 5 is provided between the aperture 4 and the photodetector 6, with the aperture 4 being disposed at a front focal position of the convergence-type collimating lens 5, and with an exit pupil 3a of the condenser lens 3 and a photosensitive surface 6a of the photodetector being located respectively at conjugate points of the convergence-type collimating lens 5. Accordingly, even if the flow particles move away in a direction perpendicular to the optical axis of the signal light detection optical system (in the up/down direction on the paper surface of FIG. 1), the signal light of the particles is incident onto the same position on the photodetector photosensitive surface 6a.

The manner of using the FIG. 1 apparatus is as follows. Particles $p_1$, such as cells or the like, previously dyed with fluorescent pigment are caused to flow into a well-known flow cell 20 in the direction perpendicular to the paper surface of FIG. 1. The particles $p_1$ flow into a flow-cell measuring flow path at the central portion of the flow cell 20 by virtue of being aligned by well-known hydrodynamic focusing.

The particles $p_1$ are irradiated with laser light from a laser light source. Although an argon laser is used as the laser light 1 in this embodiment, the present invention is not limited to this type of light source, as a helium-neon laser, or a semiconductor laser, or the like may be used. The laser light is converged through a condenser lens 2 so that the particles $p_1$ are irradiated with the converged laser light.

When the particles $p_1$ are irradiated with the laser light, the fluorescent pigment on the particles is excited so as to emit fluorescence as a signal light. The signal light from the particles $p_1$ is converged through a condenser lens 3. The signal light exits from an exit pupil 3a of the condenser lens 3 and is focused on a plane of an aperture 4 so as to form an image $p_1'$, of the particle $p_1$ thereon. The aperture 4 is provided for removing undesired light other than the signal light.

The signal light which passes through the aperture 4 is transmitted through a convergence-type collimating lens 5 and a filter 7, and is incident onto a photosensitive surface 6a of a side-on type photomultiplier tube 6. The filter 7 has filtering characteristics such that the fluorescent light is selectively transmitted therethrough.

The aperture 4 is disposed at a front (left in FIG. 1) focal position of the convergence-type collimating lens 5. Further, the exit pupil 3a and the photosensitive surface 6a are located at conjugate points of the convergence-type collimating lens 5. That is, the following expression is established among a distance S between the exit pupil 3a and the front principle point of the convergence-type collimating lens 5 with respect to the light incident from the front side, a distance S" between the photosensitive surface 6a and the rear principle point of the convergency-type collimating lens 5 with respect to the light incident from the front side, and the focal length f of the convergence-type collimating lens 5.

$$\frac{1}{S} + \frac{1}{S''} = \frac{1}{f}$$

Although the photosensitive surface of the photomultiplier tube is actually located inside the photomultiplier tube 6, the plane of an incident window surface of the tube may be regarded as the photosensitive surface 6a.

$P_2$ designates particles which have displaced by fluctuation in a direction parallel to the plane of the condenser lens and in the direction perpendicular to the flow (downward with respect to the paper surface of FIG. 1). Signal light from the particles $p_2$ (shown by broken lines in FIG. 1) is converged by the condenser lens 3 so as to be focused as an image $p_2'$, on the plane of the aperture 4. The signal light is transmitted through the convergence-type collimating lens 5 and reaches the photosensitive surface 6a of the photomultiplier tube 6.

At this time, the signal light from the particles $p_2$ and the signal light from the particles $p_1$ are projected on the same position on the photosensitive surface 6a, because the exit pupil 3a and the photosensitive surface 6a are located at the conjugate points of the convergence-type collimating lens 5. Therefore, the output signal of the photomultiplier tube 6 does not vary, even if the position of the particles fluctuates.

Although a single lens is used as the convergence-type collimating lens 5 in the foregoing embodiment of FIG. 1, the design of the convergence-type collimating lens may be suitably changed, and a compound lens may be used in place of the single lens.

Further, although fluorescence from dyed particles is used as the light for detection in the foregoing embodiment, light scattered by the flow particles may be used.

In addition, although a side-on type photomultiplier tube is used as the photodetector in the foregoing embodiment, a head-on type photomultiplier tube or other light reception elements may be used, and the design of the photodetector may be suitably changed.

As described above, the signal light detection optical system for a flow particle analysis apparatus according to the present invention uses a convergence-type collimating lens provided between the aperture and the photodetector with the aperture being disposed at the front focal position of the convergence-type collimating lens, and with the exit pupil of the condenser lens and the photosensitive surface of the photodetector being located at the conjugate points of the convergence-type collimating lens respectively Therefore, the signal light detection optical system according to the present invention has the advantage that little variation is caused in the output of the photodetector even if the position of the flowing particles fluctuates.

Although a preferred embodiment of the invention has been described and illustrated, it should be apparent that many modifications can be made thereto without departing from the spirit and scope of the invention. Accordingly, the invention is not limited by the foregoing description, but is only limited by the scope of the appended claims

I claim:

1. An optical system for signal light detection of a flow particle comprising:
   means for directing light onto flow particles flowing in a flow cell; a condenser lens for condensing signal light emitted from the flow particles, a photodetector for receiving signal light exiting from said condenser lens, an aperture provided between said condenser lens and said photodetector for removing undesired light, and a convergence-type collimating lens provided between said aperture and said photodetector, said aperture being disposed at a front focal position of said convergence-type collimating lens, and an exit pupil of said condenser lens and a photosensitive surface of said photodetector being located respectively at conjugate points of said convergence-type collimating lens, whereby the photosensitive surface of said photodetector is located at the image of said exit pupil.

2. An optical system as in claim 1, wherein said light directing means comprises a source of laser light.

3. An optical system as in claim 1, further comprising a light filter provided between said convergence-type collimating lens and said photodetector for selectively transmitting light therethrough.

4. An optical system as in claim 1, wherein said convergence-type collimating lens is a single lens.

5. An optical system as in claim 1, wherein said convergence-type collimating lens is a compound lens.

* * * * *